United States Patent [19]

Katsuro et al.

[11] Patent Number: 5,574,172

[45] Date of Patent: Nov. 12, 1996

[54] PROCESS FOR PRODUCING HALOGENATED PHTHALIC ANHYDRIDE

[75] Inventors: Yoshio Katsuro; Hitoshi Matsuda, both of Kitakyushu, Japan

[73] Assignee: Mitsubishi Chemical Corporation, Japan

[21] Appl. No.: 250,787

[22] Filed: May 26, 1994

[30] Foreign Application Priority Data

May 27, 1993 [JP] Japan .................................. 5-126263

[51] Int. Cl.$^6$ .......................... C07D 307/89; C07B 39/00
[52] U.S. Cl. .............................................................. 549/246
[58] Field of Search ............................................. 549/246

[56] References Cited

U.S. PATENT DOCUMENTS

| | | | |
|---|---|---|---|
| 2,429,985 | 11/1947 | Blume et al. | 549/246 |
| 3,240,792 | 3/1966 | Patrick | 549/246 |
| 3,308,069 | 3/1967 | Wadlinger et al. | 252/455 |
| 3,480,667 | 11/1969 | Siegart et al. | 549/246 |
| 3,956,321 | 5/1976 | Markezich | 549/246 |
| 4,297,283 | 10/1981 | Verbicky | 549/246 |
| 4,517,372 | 5/1985 | Tang | 549/246 |
| 4,709,056 | 11/1987 | Cotter et al. | 549/246 |
| 4,785,121 | 11/1988 | Leone-Bay et al. | 549/246 |
| 5,003,088 | 3/1991 | Spohn et al. | 549/246 |
| 5,049,682 | 9/1991 | Tang et al. | 549/246 |
| 5,059,697 | 10/1991 | Fentel et al. | 549/246 |
| 5,206,391 | 4/1993 | Seper et al. | 549/246 |
| 5,233,054 | 8/1993 | Tang et al. | 549/246 |
| 5,288,879 | 2/1994 | Bottelberghe et al. | 549/246 |
| 5,300,201 | 4/1994 | Seper et al. | 549/246 |
| 5,322,954 | 6/1994 | Seper et al. | 549/246 |
| 5,384,413 | 1/1995 | Pfirmann et al. | 549/246 |

FOREIGN PATENT DOCUMENTS

| | | | |
|---|---|---|---|
| 0258726 | 3/1988 | European Pat. Off. | |
| 334049 | 9/1989 | European Pat. Off. | 549/246 |
| 338215 | 10/1989 | European Pat. Off. | 549/246 |
| 3130033 | 2/1983 | Germany . | |
| 3228270 | 2/1984 | Germany . | |
| 3339235 | 5/1985 | Germany . | |
| 3911951 | 11/1989 | Germany . | |
| 3911951A | 11/1989 | Germany . | |
| 60-161974 | 8/1985 | Japan . | |
| 1118378 | 6/1986 | Japan | 549/246 |
| 62-185082 | 8/1987 | Japan . | |
| 4-368340 | 12/1992 | Japan . | |
| 5-976 | 1/1993 | Japan . | |
| 1004328 | 3/1983 | U.S.S.R. . | |
| 631008 | 10/1949 | United Kingdom . | |

Primary Examiner—Cecilia Tsang
Attorney, Agent, or Firm—Nixon & Vanderhye

[57] ABSTRACT

The disclosure describes a process for producing halogenated phthalic anhydride, which comprises reacting phthalic anhydride with a molecular halogen in vapor phase in the presence of a catalyst containing zeolite as active component.

24 Claims, No Drawings

PROCESS FOR PRODUCING HALOGENATED PHTHALIC ANHYDRIDE

BACKGROUND OF THE INVENTION

The present invention relates to a process for producing halogenated phthalic anhydride. More particularly, it relates to a process for halogenating, especially chlorinating, phthalic anhydride in a vapor phase at elevated temperature.

Halogenated phthalic anhydride is utilized as an intermediate for the synthesis of medicines, agricultural chemicals and synthetic resin materials. Usually halogenated phthalic anhydride is produced by a process in which phthalic anhydride is dissolved in an alkaline aqueous solution to form an alkali metal salt of phthalic acid and halogen gas is introduced into the aqueous solution for halogenation.

According to this method, however, since halogenation is carried out in aqueous solution, and halogenated phthalic acid is produced as reaction product, it is necessary to carry out a separation of the halogenated phthalic acid from the aqueous solution and a dehydration reaction of the halogenated phthalic acid into halogenated phthalic anhydride. Therefore, this process is complicated and is time-consuming, and also the treatment of the waste water discharged from the separation step in large quantities, is very troublesome. Further, the result of the halogenation reaction itself is not well satisfactory. Methods for chlorinating phthalic anhydride in a vapor phase without using a catalyst have been known (U.S. Pat. No. 4,297,283), but these methods involved the serious problems such as corrosion of the apparatus since the reaction is carried out at a high temperature.

In view of the above circumstances, the present inventors gave their attention on the fact that vapor-phase halogenation of phthalic anhydride is advantageous over liquid-phase reaction as the reaction process is greatly simplified and also troublesome waste water is not generated. However, the conventional non-catalytic vapor-phase reactions are carried out at a very high temperature which is above 400° C. Also, the desired halogenated product can hardly be obtained when the reaction is carried out at a low temperature, especially below 350° C. The present invention, therefore, is intended to provide a process for halogenating phthalic anhydride in a vapor phase at a relatively low temperature.

As a result of the present inventors' strenuous researches for solving the above technical problems, it has been found that by reacting phthalic anhydride and a molecular halogen in a vapor phase in the presence of a catalyst containing zeolite as an active component, it is possible to remarkably simplify the reaction process and to produce halogenated phthalic anhydride efficiently at a relatively low temperature without dehydration and discharge of a large quantity of waste water. The present invention has been attained on the basis of this finding.

SUMMARY OF THE INVENTION

An object of the present invention is to provide a process for producing halogenated phthalic anhydride by directly reacting phthalic anhydride and a halogen, the reaction process being remarkably simplified.

Another object of the present invention is to provide a process for producing halogenated phthalic anhydride efficiently at a relatively low temperature.

To accomplish the aims, in a first aspect of the present invention, there is provided a process for producing halogenated phthalic anhydride, in which phthalic anhydride is reacted with a molecular halogen in a vapor phase in the presence of a catalyst containing zeolite.

In a second aspect of the present invention, there is provided a preparation of monohalogenophthalic anhydrides such as 3-monohalogenophthalic anhydride and 4-monohalogenophthalic anhydride.

DETAILED DESCRIPTION OF THE INVENTION

In the present invention, phthalic anhydride is halogenated with a molecular halogen. As the molecular halogen, usually molecular chlorine or molecular bromine are used. Among them, molecular chlorine is preferred. Theoretically, one mole of molecular halogen is necessary to produce one mole of monohalogenophthalic anhydride and two mole of halogen for one mole of dihalogenophthalic anhydride. But in the present invention, the molecular halogen is used in an amount which is 0.2 to 10 times of the theoretical amount, preferably 0.5 to 5 times of the theoretical amount. If the amount of the molecular halogen is less than 0.2 times of the theoretical amount, a halogenation reaction does not proceed efficiently. On the other hand, if the one is more than 10 times, it is disadvantageous in economy as an industrial process. In the present invention, presence of oxygen and water in the reaction system is undesirable, so that it is recommended to maintain the oxygen concentration of not more than 1 vol % and water vapor concentration substantially zero, that is preferably not more than 0.01 wt %, in the reaction zone atmosphere.

In the present invention, it is essential to use zeolite as a catalyst. Zeolite used as a catalyst in the present invention is typically a composition represented by the following formula:

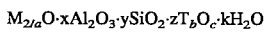

wherein M represents at least one kind of cation with 'a' valency; T represents at least one member selected from the group consisting of chromium, gallium, titanium, boron, iron, lead, tin, copper, indium, cobalt, nickel, zinc, vanadium, molybdenum, arsenic, antimony, manganese, germanium, silver, lanthanum, cadmium, magnesium, cerium and phosphorus; and x, y, z, b, c and k are each a positive number including 0.

Zeolite has a crystalline structure. Aluminosilicates (z=0) which are the most typical example of zeolite, have a rigid three-dimensional reticulate structure composed of $SiO_4$ tetrahedron and $AlO_4$ tetrahedron, which are bound to each other through oxygen atoms in the structure. The ratio of the number of oxygen atoms to the total number of aluminum atoms and silicon atoms is 1:2. The aluminosilicates used in the present invention as a catalyst are preferably in the range of x=0.1–2, y=1–300, z=0–1.5, k=0–40, and y/x=0.5–1,000. Of course, aluminosilicates outside the above-specified ranges may be used.

Examples of aluminosilicate-type zeolites usable in the present invention include faujasite-type zeolites popularly known as zeolite X or zeolite Y; zeolite beta; ZSM-5; zeolite omega; zeolite L; offretite/erionite; and mordenite. Molecular sieves such as 13X are also usable as zeolite in the present invention.

In the present invention, it is also recommended to use so-called metalloaluminosilicates of the above-shown formula wherein z is a positive number other than 0, in which aluminum and/or silicon in the zeolite skeleton are isomorphously replaced by other metals. Of these metalloaluminosilicates, those having a zeolite beta-type structure are preferred. The metals usable for the said isomorphous replacement include those shown as T in the above formula, of which boron, iron, lead, tin, indium, cobalt, zinc, germanium, gallium and cadmium are preferred. In the present invention, the metals having valence (valency) of 2 or 3 may preferably be used. Among them, zinc is especially preferred. These metalloaluminosilicates having a zeolite beta skeleton can be produced by, for example, a process disclosed in U.S. Pat. No. 3,308,069. According to this process, the metal used for isomorphous replacement of aluminum and/or silicon in the zeolite skeleton is added as an inorganic acid salt such as nitrate or sulfate or an organic acid salt such as acetate in a suitable amount to provide a desired composition in the material for producing zeolite beta, and the resultant mixture is subjected to hydrothermal synthesis to form the objective metalloaluminosilicate having a zeolite beta skeleton. In the present invention, the aluminosilicates which are produced by conventional hydrothermal synthesis can also be used. In the present invention, it is also possible to use zeolite (metalloaluminosilicates and aluminosilicates), which is obtained from the said hydrothermal synthesis and subjected to a conventional dealuminization treatment to change the silica/alumina ratio. In the following, the word "zeolite", unless it is marked especially, means both of metalloaluminosilicates and aluminosilicates.

Zeolite is electrically equilibrated by cations (M). Zeolite produced from hydrothermal synthesis usually has sodium ions or potassium ions as cations (M). In the present invention, these sodium-type or potassium-type zeolites may be used for the reaction in the form as they are, but the zeolites in which sodium ions or potassium ions have been cation-exchanged with the ions of a metal such as zinc, gallium, iron, cobalt, copper, cadmium, nickel, magnesium, calcium, rubidium, cerium, strontium, barium, indium, chromium, titanium, tin, lead and manganese, can be also favorably used. The pore radii of zeolite are affected by the exchangeable cations contained therein. Cations having large ion radii reduce the pore radii of zeolite when they are used for a cation exchange reaction. In the present invention, zeolites exchanged with cations having ion radii (van der Waals radii) in the range of 0.55 to 0.95 Å are preferably used, which include ions of zinc, magnesium, manganese, iron, cobalt, nickel, gallium, indium, chromium, titanium, tin, lead, and so on. Among these cations, zinc ion is most preferred. Especially the ones in which 1 to 95 mol %, preferably 10 to 50 mol % of exchangeable sodium and potassium have been exchanged with zinc are preferred. As the zeolites to be subjected to cation exchange with zinc, zeolite X, ZSM-5, zeolite L, zeolite omega, mordenite, offretite/erionite, zeolite beta and the like are preferred in view of heat resistance and acid resistance. Among them, ZSM-5 and zeolite beta are preferred in view of reaction activity. Those having a zeolite beta skeleton are especially preferred.

Cation exchange with metal ions can be accomplished by a known method. Usually, such cation exchange is performed by adding zeolite in an aqueous solution of a metal salt and allowing the solution to stand still for 10 minutes to 48 hours. As the zinc salts generally used for cation exchange with zinc, the zinc salts of organic acids such as zinc acetate and zinc oxalate, and the zinc salts of inorganic acids such as zinc sulfate, zinc nitrate and zinc chloride can be exemplified. The concentration of the zinc salt in the solution is usually in the range of $10^{-4}$ to 10 mol/liter, preferably $10^{-2}$ to 5 mol/liter. The exchange reaction temperature is selected from the range of 10° to 100° C., preferably 20° to 80° C. For accelerating the exchange reaction, it is recommended to carry out the exchange reaction at a high temperature within the said range.

The zeolite used as catalyst in the present invention may be proton type zeolite in which the cation has been converted into proton type. The conversion of cation into proton can be accomplished by a known method. For example, ammonium type zeolite, in which cation is exchanged with ammonium ion, is subjected to calcination.

The zeolite used in the present invention is preferably one having a pore inlet diameter of 4 to 20 Å, more preferably 5 to 9 Å. In view of molecular size of the reactant phthalic anhydride and the reaction product, use of zeolite beta is preferred in case of producing 4-monohalogenophthalic anhydride. Zeolite beta obtained by cation exchange with zinc or isomorphous replacement with zinc is especially preferred in view of catalyst activity.

The $SiO_2/Al_2O_3$ ratio in zeolite used in the present invention may be selected within wide range, but it is not more than $10^4$, preferably 0.5 to $10^3$.

Zeolite is generally produced as a crystalline fine powder, and it is usually mixed with binder and molded in a size of about 1 to 100 mm. Any binder which is inactive to the reaction may be used, but usually inorganic oxides such as alumina, titania, chromia, magnesia, silica, clay or the like is used.

The content of the zeolite in the molded zeolite catalyst is usually 10 to 90% by weight. A content in the range of 10 to 50% by weight is preferred in view of heat resistivity of the catalyst. The molded zeolite catalyst is usually in the form of granules or pellets having a size of about 1 to 100 mm. In the present invention, the commercially available fine-powdery zeolite catalysts can be used in the form as they are, but it is of course possible to use molded commercial catalysts.

In the present invention, it is preferable that zeolite catalysts are dried or calcined so as to have substantially no water before being used for reaction. Thus zeolite catalysts are heated and calcined in an atmosphere of an inert gas such as nitrogen gas, helium gas, argon gas and so on, or a hydrogen gas at a temperature of 100° to 1300° C., preferably 100° to 600° C. Further, it is preferred that zeolite catalysts are contacted with a halogen gas, preferably at an elevated temperature of 100° to 600° C. before being used for the reaction. The amount of the halogen gas used above is not less than 0.001 Nl/g-catalyst, preferably 0.01 to 1 Nl/g-catalyst.

In the present invention, phthalic anhydride and a molecular halogen are reacted in a vapor phase in the presence of the said zeolite catalyst. The reaction temperature is usually 150° to 280° C., preferably 180° to 280° C. When the reaction temperature is too low, the halogenation reaction may be unable to proceed smoothly, while when the reaction temperature is too high, side reactions tend to take place, and also an expensive material is required for the reaction apparatus.

The reaction may be carried out by either fixed bed or fluidized bed, but the former is preferred. In carrying out the reaction of the present invention, phthalic anhydride gas generated from the heated and melted phthalic anhydride, and halogen gas are supplied simultaneously into a reactor filled with the said catalyst, and maintained at a prescribed temperature. If necessary, an inert gas may be supplied into the reactor to properly adjust the reactant concentration in the reactor. Inert gas may be separately introduced into the reactor, but it is preferably introduced along with phthalic anhydride. By introducing the inert gas into the reactor through an evaporator wherein molten phthalic anhydride is contained, it is possible to supply both phthalic anhydride gas and inert gas simultaneously into the reactor.

The reaction time in the process of the present invention varies depending on the reaction form. For example, in the case of the flow-type reaction in which the reactant gas is continuously introduced into a fixed catalyst bed, and which is the most ordinary type, the reaction is carried out at a space velocity (GHSV) of usually about 1/10 to 10,000, preferably about 1/1 to 1,000.

According to the process of the present invention, 3-halogenophthalic anhydride and 4-halogenophthalic anhydride can be produced very efficiently, so that it is recommended to apply the present invention to the production of these monohalogenophthalic anhydrides.

According to the present invention, since halogenation can be accomplished by directly reacting phthalic anhydride with a halogen, the reaction process is remarkably simplified. The reaction temperature is lower than in the conventional vapor phase halogenation process, and the objective halogenated phthalic anhydride can be obtained efficiently.

EXAMPLES

The present invention is further illustrated below with reference to the examples. These examples, however, are merely intended to be illustrative and not to be construed as limiting the scope of the invention in any way.

EXAMPLE 1

5 g of a commercial zeolite catalyst (Zeolum F-9) was filled in a quartz-made reaction tube (inner diameter: 20 mm, length: 250 mm) and heated to 300° C. under a nitrogen stream in an electric furnace. After the temperature has been stabilized, flow of nitrogen gas was stopped and then chlorine gas was flown into the reaction tube at a rate of 1.6 liter/hr for 30 minutes.

Then the flow rate of chlorine gas was adjusted to 0.8 liter/hr. In the meantime, phthalic anhydride (6.6 g, 44.6 mmol) was supplied into an evaporator and melted by heating to 280° C. Also, nitrogen gas was introduced into the reaction tube through the evaporator at a rate of 2.2 liter/hr, and the phthalic anhydride gas generated in the evaporator was supplied along with the said nitrogen gas into the reaction tube. The whole amount of melted phthalic anhydride was supplied into the reaction tube in 60 minutes. The contact time of the reactants with the catalyst layer was 3.4 seconds.

After the finish of the reaction, the reaction product was dissolved in acetone and subjected to quantitative analysis by gas chromatography. The conversion of phthalic anhydride to halogenated phthalic anhydride was 39.7%, and the selectivity of monochloro-phthalic anhydride was 81.8%.

EXAMPLES 2–6

A mixture of 20 wt % of commercial zeolite and 80 wt % of anatase type titania was molded by compression. The molded product was crushed and sifted, with the particles which did not pass through a 24 mesh-sieve of JIS Standard, being collected for use as catalyst. By using this catalyst, the same vapor-phase chlorination reaction as Example 1 was carried out. The results are shown in Table 1.

EXAMPLE 7

The procedure of Example 1 was carried out except that the reaction temperature was set at 200° C. The conversion of phthalic anhydride to halogenated phthalic anhydride was 14.0%, and the selectivity of monochloro-phthalic anhydride was 85.6%.

COMPARATIVE EXAMPLE 1

The same procedure as shown in Example 1 was carried out except that no zeolite catalyst was used. The results are shown in Table 1.

COMPARATIVE EXAMPLE 2

The same procedure as shown in Example 1 was carried out except that titania was used in place of zeolite catalyst. The results are shown in Table 1.

TABLE 1

| | Catalyst used | Binder | Conversion (%) |
|---|---|---|---|
| Example 1 | X-type zeolite[1] | None | 39.7 |
| Example 2 | X-type zeolite[2] | $TiO_2$ | 15.2 |
| Example 3 | Y-type zeolite[3] | $TiO_2$ | 9.4 |
| Example 4 | Zeolite omega | $TiO_2$ | 6.3 |
| Example 5 | Offretite/erionite[4] | $TiO_2$ | 5.5 |
| Example 6 | Beta-type zeolite[5] | $TiO_2$ | 5.9 |
| Example 7 | X-type zeolite[1] | $TiO_2$ | 14.0 |
| Comp. Example 1 | No catalyst | None | 1.2 |
| Comp. Example 2 | No catalyst | $TiO_2$ | 2.6 |

(Note)
[1]: Zeolum F-9 product of Tosoh Co., Ltd. ($Na^+$ type, spherical, 9–14 meshes of JIS Standard, pore diameter: approx. 8.5Å, binder: clay)
[2]: Zeolum F-9 product of Tosoh Co., Ltd. ($Na^+$ type, powdery, passing through 100 mesh-sieve of JIS Standard, pore diameter: approx. 8.5Å)
[3]: HSZ-320-NAD product of Tosoh Co., Ltd. ($Na^+$ type, pellets, pore diameter: approx. 7.4Å, used after ground by mortar)
[4]: Offretite/erionite product of Tosoh Co., Ltd. ($Na^+$ type, powdery, pore diameter: approx. 6Å*)
*: Pore diameter of offretite. An Offretite/erionite mixture produced together and sold as such (without separation) was used.
[5]: Beta-type zeolite product of PQ Corp. ($Na^+$ type, powdery, pore diameter: approx. 7Å)

| | Selectivity of monochloro-form | Contact time (sec) |
|---|---|---|
| Example 1 | 81.8 | 3.4 |
| Example 2 | 71.2 | 4.9 |
| Example 3 | 87.8 | 3.4 |
| Example 4 | 85.4 | 4.7 |
| Example 5 | 65.0 | 4.9 |
| Example 6 | 84.8 | 5.0 |
| Example 7 | 85.6 | 4.6 |
| Comp. Example 1 | 88.3 | 3.6 |
| Comp. Example 2 | 91.0 | 7.0 |

EXAMPLE 8

5.0 g of the same zeolite X powder as used in Example 2 was immersed in 300 ml of a 0.2M aqueous solution of zinc acetate [$Zn(O_2CCH_3)_2 \cdot 2H_2O$] at room temperature for about 12 hours to exchange part of exchangeable cations ($Na^+$) with zinc ion.

By using the thus obtained zinc ion-exchanged zeolite, a catalyst was prepared in the same way as Examples 2–6, and the same vapor phase chlorination reaction as Example 1 was carried out by using 12 g of the said catalyst. The results are shown in Table 2.

EXAMPLES 9–21

The same procedure as shown in Example 8 was carried out except for use of 12 g of X-type zeolite subjected to cation exchange with ions of K, Fe, Co, Cu, Cd, Rb, Cs, Mg, Ca, Sr, Ba, Mn or Ni in place of Zn ion. In the case of the Ca ion-exchanged zeolite of Example 17, there was used 5.0 g of catalyst. The results are shown in Table 2.

EXAMPLE 22

The same procedure as shown in Example 1 was carried out except that zeolite X carrying sodium chloride, prepared by supplying zeolite X which was the same as used in Example 1, into a saline solution and evaporating the solution to dryness, was used without molding in an amount of 5 g as catalyst. The results are shown in Table 2.

TABLE 2

| | Zeolite catalyst | Cation exchanged |
|---|---|---|
| Example 8 | Zeolum F-9 (X type) produced by Tosoh | Zn |
| Example 9 | Zeolum F-9 (X type) produced by Tosoh | K |
| Example 10 | Zeolum F-9 (X type) produced by Tosoh | Fe |
| Example 11 | Zeolum F-9 (X type) produced by Tosoh | Co |
| Example 12 | Zeolum F-9 (X type) produced by Tosoh | Cu |
| Example 13 | Zeolum F-9 (X type) produced by Tosoh | Cd |
| Example 14 | Zeolum F-9 (X type) produced by Tosoh | Rb |
| Example 15 | Zeolum F-9 (X type) produced by Tosoh | Cs |
| Example 16 | Zeolum F-9 (X type) produced by Tosoh | Mg |
| Example 17 | Zeolum F-9 (X type) produced by Tosoh | Ca |
| Example 18 | Zeolum F-9 (X type) produced by Tosoh | Sr |
| Example 19 | Zeolum F-9 (X type) produced by Tosoh | Ba |
| Example 20 | Zeolum F-9 (X type) produced by Tosoh | Ni |
| Example 21 | Zeolum F-9 (X type) produced by Tosoh | Mn |
| Example 22 | Zeolum F-9 (X type) produced by Tosoh | Carrying NaCl |

| | Cation exchange ratio (%) | Conversion (%) | Selectivity of monochloro-form (%) |
|---|---|---|---|
| Example 8 | 40 | 33.6 | 77.9 |
| Example 9 | 40 | 17.9 | 85.9 |
| Example 10 | 40 | 22.5 | 77.2 |
| Example 11 | 40 | 17.8 | 84.7 |
| Example 12 | 40 | 17.4 | 67.7 |
| Example 13 | 40 | 12.8 | 83.3 |
| Example 14 | 40 | 15.3 | 86.8 |
| Example 15 | 40 | 8.6 | 89.5 |
| Example 16 | 40 | 9.1 | 87.6 |
| Example 17 | 40 | 9.5 | 69.7 |
| Example 18 | 40 | 4.4 | 80.0 |
| Example 19 | 40 | 4.6 | 69.0 |
| Example 20 | 70 | 7.0 | 76.3 |
| Example 21 | 40 | 7.1 | 80.6 |
| Example 22 | 40 | 9.3 | 82.0 |

EXAMPLE 23

The same procedure as shown in Example 1 was carried out except for use of 12 g of zeolite prepared by exchanging a part of Na ions of zeolite beta which was the same as used in Example 6, with zinc ions as in the same way as shown in Example 8. Fourty percentage of the exchangeable cation of the zeolite beta was exchanged with zinc ions. The space velocity in the reaction was 740. The results are shown in Table 3.

EXAMPLES 24–28

The same procedure as shown in Example 1 was carried out except for use of 12 g of zeolite catalyst, ZSM-5 (produced by Mitsubishi Kasei Corp.), mordenite (produced by Tosoh Co., Ltd. ), L-type zeolite (produced by Tosoh Co., Ltd.), zeolite omega (the same one used in Example 4) and offretite/erionite (the same one used in Example 5). The cation of these zeolite catalysts were exchanged with zinc ion before use in the same way as shown in Example 8. The results are shown in Table 3.

TABLE 3

| | Zeolite catalyst | Cation exchanged |
|---|---|---|
| Example 23 | Beta (produced by PQ Corp.) | Zn |
| Example 24 | ZSM-5 | Zn |
| Example 25 | Mordenite (produced by Tosoh Co., Ltd.) | Zn |
| Example 26 | Zeolite L (produced by Tosoh Co., Ltd.) | Zn |
| Example 27 | Zeolite omega | Zn |
| Example 28 | Offretite/erionite | Zn |

| | Cation exchange ratio (%) | Conversion (%) | Selectivity of monochloro-form (%) |
|---|---|---|---|
| Example 23 | 40 | 33.8 | 83.1 |
| Example 24 | 40 | 13.6 | 77.6 |
| Example 25 | 40 | 1.9 | 92.2 |
| Example 26 | 40 | 3.0 | 90.6 |
| Example 27 | 40 | 2.4 | 91.7 |
| Example 28 | 40 | 3.1 | 92.6 |

EXAMPLE 29

The same procedure as shown in Example 1 was carried out except for use of 12 g of catalyst prepared by conducting the same cation exchange treatment as shown in Example 8 wherein zinc chloride was used in place of zinc acetate and the zinc ions exchange ratio was 23%. The results are shown in Table 4.

EXAMPLE 30

The same procedure of Example 1 was carried out except for use of 12 g of catalyst prepared by conducting the same exchange treatment as shown in Example 8 wherein zinc sulfate [$Zn(SO_4$)·$7H_2O$] was used in place of zinc acetate and the zinc ions exchange ratio was 27%. The results are shown in Table 4.

EXAMPLE 31

The same procedure as shown in Example 1 was carried out except for use of 12 g of catalyst prepared by conducting the same exchange treatment as shown in Example 8 wherein zinc nitrate [$Zn(NO_3)_2$·$6H_2O$] was used in place of zinc acetate and the exchange zinc ions ratio was 27%. The results are shown in Table 4.

EXAMPLE 32

The same procedure as shown in Example 1 was carried out except for use of 12 g of catalyst prepared by conducting the same exchange treatment as shown in Example 8 wherein zinc acetate [$Zn(O_2CCH_3)_2 \cdot 2H_2O$] was used and the zinc ions exchange ratio was 29%. The results are shown in Table 4.

EXAMPLES 33–34

The same procedure as shown in Example 1 was carried out except for use of 12 g of catalyst prepared by conducting the same exchange treatment as shown in Example 8 wherein zinc acetate [$Zn(O_2CCH_3)_2 \cdot 2H_2O$] was used and the zinc ions exchange ratio was 10% and 4%, respectively. The results are shown in Table 4.

EXAMPLE 35

The same procedure as shown in Example 34 (zinc ions exchange ratio of the catalyst was 10%) was carried out except that the reaction was carried out by supplying phthalic anhydride along with chlorine gas (2.0 l/hr), instead of supplying it with nitrogen gas. The space velocity (GHSV) was 510. The results are shown in Table 4.

EXAMPLE 36

The same procedure as shown in Example 36 was carried out except that the chlorine gas flow rate was set at 6.0 l/hr and the space velocity (GHSV) at 1,290. The results are shown in Table 4.

EXAMPLE 37

The same procedure as shown in Example 34 was carried out except that the catalyst was not contacted with chlorine gas before use. The results are shown in Table 4.

TABLE 4

| | Zeolite catalyst | Cation exchanged |
|---|---|---|
| Example 29 | Beta type (produced by PQ Corp.) | Zn/$ZnCl_2$ |
| Example 30 | Beta type (produced by PQ Corp.) | Zn/$ZnSO_4 \cdot 7H_2O$ |
| Example 31 | Beta type (produced by PQ Corp.) | Zn/$Zn(NO_3)_2 \cdot 6H_2O$ |
| Example 32 | Beta type (produced by PQ Corp.) | Zn/$Zn(O_2CCH_3)_2 \cdot 2H_2O$ |
| Example 33 | Beta type (produced by PQ Corp.) | Zn/$Zn(O_2CCH_3)_2 \cdot 2H_2O$ |
| Example 34 | Beta type (produced by PQ Corp.) | Zn/$Zn(O_2CCH_3)_2 \cdot 2H_2O$ |
| Example 35 | Beta type (produced by PQ Corp.) | Zn/$Zn(O_2CCH_3)_2 \cdot 2H_2O$ |
| Example 36 | Beta type (produced by PQ Corp.) | Zn/$Zn(O_2CCH_3)_2 \cdot 2H_2O$ |
| Example 37 | Beta type (produced by PQ Corp.) | Zn/$Zn(O_2CCH_3)_2 \cdot 2H_2O$ |

| | Cation exchange ratio (%) | Conversion (%) | Selectivity of monochloro-form (%) |
|---|---|---|---|
| Example 29 | 23 | 28.3 | 89.0 |
| Example 30 | 27 | 23.2 | 89.6 |
| Example 31 | 27 | 35.8 | 86.2 |
| Example 32 | 29 | 31.6 | 86.9 |
| Example 33 | 10 | 24.8 | 91.0 |
| Example 34 | 4 | 15.3 | 91.1 |
| Example 35 | 10 | 39.5 | 89.6 |
| Example 36 | 10 | 56.1 | 80.0 |
| Example 37 | 10 | 17.1 | 90.2 |

EXAMPLE 38

A zinc-containing beta-type metalloaluminosilicate wherein zinc is taken in the skeleton of beta zeolite by isomorphous replacement (hereinafter referred to as zinc beta) was prepared in the following way.

6.95 g of $NaAlO_2$ (product of Wako Pure Chemicals Co., Ltd., Al/NaOH=0.54), 4.47 g of $Zn(NO_3)_2 \cdot 6H_2O$ (product of Kishida Chemical Co., Ltd.) and 121.12 g of demineralized water were fed into a 300 ml plastic-beaker and stirred for 20 minutes. To the resultant solution was added 61.6 g of a 40% aqueous solution of tetraethylammonium hydroxide (TEA·OH, product of Aldrich Ltd.), followed by 10-minute stirring. The resulting solution is called as "solution A". 45.1 g of finely powdered silica (TOKUSIL-U, product of Tokuyama Soda Co., Ltd.) was fed into a one-liter widemouthed plastic-beaker, and the solution A was added thereto. Then 62.1 g of demineralized water was added to the beaker, and the mixture was stirred by a homogenizer at 7,000 r.p.m. for 10 minutes to homogenize the mixture. This mixture had the following composition: $SiO_2/Al_2O_3$=25, $OH^-/SiO_2$=0.29, $H_2O/SiO_2$=16.3, $Na/SiO_2$=0.148, $TEA/SiO_2$ =0.22, $SiO_2/ZnO$=49.9. The mixture was transferred into a Teflon-made vessel and loaded in a one-liter SUS-316 autoclave. After replacing the atmosphere in the autoclave with nitrogen, the hydrothermal synthesis started while stirring the mixture in the vessel at 180 r.p.m. The temperature of the autoclave was raised (at a rate of 0.4° C./min) from room temperature to 160° C. and maintained at 160° C. for 90 hours. After the hydrothermal synthesis was completed, the content in the autoclave was filtered, washed with demineralized water and dried at 120° C. for a whole day and night. There was obtained 46.3 g of a dried product. Powder X-ray diffraction analysis of the product showed a diffraction pattern of zeolite beta with no peak attributable to the oxide of zinc, and the objective zinc beta was produced. The cation of the zinc beta was converted to proton by a conventional method.

The same procedure as shown in Example 1 was carried out except for use of a catalyst prepared in the above. The results are shown in Table 5.

TABLE 5

| | Zeolite catalyst | Cation |
|---|---|---|
| Example 39 | Zinc beta (β-type zinc aluminosilicate) | H |
| Comp. Example 9 | No catalyst ($TiO_2$ alone) | — |
| Comp. Example 8 | No catalyst (No $TiO_2$) | — |

| | Cation exchange ratio (%) | Conversion (%) | Selectivity of monochloro-form (%) |
|---|---|---|---|
| Example 39 | 100 | 9.7 | 95.6 |
| Comp. Example 1 | — | 2.6 | 91.0 |

TABLE 5-continued

| | | | |
|---|---|---|---|
| Comp. Example 2 | — | 1.2 | 88.3 |

COMPARATIVE EXAMPLES 3–6

The same procedure as shown in Example 1 was carried out except for use of 5.0 g of active carbon, 6.1 g of active carbon which contains 23.6 wt % of calcium chloride, 5.0 g of silica alumina ($SiO_2/Al_2O$=0.09) and 5.0 g of silica alumina ($SiO_2/Al_2O_3$=10.8), respectively, in place of zeolite. All of them gave lower conversion and selectivity of monochloro-phthalic anhydride than zeolite X. Further, in case of zeolite, the material balance between phthalic anhydride introduced into the reactor and reaction mixture discharged from the reactor was almost attained, but in case the above catalysts were used, a substantial portion of the reactants was adsorbed on the catalyst and the material balance was not attained.

What is claimed is:

1. A process for producing halogenated phthalic anhydride, which comprises reacting phthalic anhydride with a molecular halogen in vapor phase at a temperature in the range of 150° C. to about 280° C. and in the presence of a catalyst containing zeolite as active component, and the zeolite is cation exchanged with zinc ion.

2. A process for producing halogenated phthalic anhydride, which comprises reacting phthalic anhydride with a molecular halogen in vapor phase at a temperature in the range of 150° C. to about 280° C. and in the presence of a catalyst containing zeolite as active component, and the zeolite is zeolite X which is cation exchanged with an ion selected from the group consisting of ions of Zn, K, Fe, Co and Rb.

3. A process for producing halogenated phthalic anhydride, which comprises reacting phthalic anhydride with a molecular halogen in vapor phase at a temperature in the range of 150° C. to about 280° C. and in the presence of a catalyst containing zeolite as an active component, wherein the zeolite is selected from the group consisting of zeolite X, zeolite Y, zeolite omega and zeolite beta.

4. A process for producing halogenated phthalic anhydride, which comprises reacting phthalic anhydride with a molecular halogen in vapor phase at a temperature in the range of 150° C. to about 280° C. and in the presence of a catalyst containing zeolite as an active component, wherein the zeolite is zeolite beta which is isomorphously replaced with Zn.

5. The process according to any one of claims 1, 2, 3 or 4, wherein the molecular halogen is molecular chlorine or molecular bromine.

6. The process according to any one of claims 1, 2, 3 or 4, wherein the oxygen concentration is not more than 1 vol %, and the water vapor concentration is not more than 0.01 wt % in the atmosphere of the reaction zone.

7. The process according to claim 3, wherein the zeolite has sodium ions or potassium ions as cations.

8. The process according to claim 1, wherein the zeolite has a zeolite beta skeleton.

9. The process according to claim 1, wherein the zeolite is the one in which 1 to 95% of exchangeable cations are cation-exchanged with zinc ions.

10. The process according to any one of claims 1, 2, 3 or 4, wherein the catalyst is molded zeolite catalyst containing an inorganic oxide inert to the reaction as a binder.

11. The process according to any one of claims 1, 2, 3 or 4, wherein the catalyst is zeolite moldings prepared using titania as binder.

12. The process according to claim 11, wherein the content of zeolite in the catalyst is 10 to 90 wt %.

13. The process according to any one of claims 1, 2, 3 or 4, wherein the reaction is carried out at 150° to 400° C.

14. The process according to any one of claims 1, 2, 3 or 4, wherein the reaction is carried out at 180° to 200° C. by supplying a halogen gas mixed with phthalic anhydride and inert gas, into a fixed bed of zeolite catalyst.

15. The process according to any one of claims 1, 2, 3 or 4, wherein the reaction is carried out at a space velocity of 1/10 to 10,000.

16. The process according to any one of claims 1, 2, 3 or 4, wherein the catalyst is contacted with a halogen gas at elevated temperature of 100° to 600° C. prior to the reaction.

17. The process according to any one of claims 1, 2, 3 or 4, wherein the zeolite has a pore inlet diameter at ordinary temperature of 4 to 20 Å.

18. The process according to claim 1, wherein the zeolite is zeolite beta which is cation exchanged with zinc ion.

19. The process according to claim 1, wherein the zeolite is zeolite X which is cation exchanged with zinc ion.

20. The process according to claim 1, wherein the zeolite is zeolite omega which is cation exchanged with zinc ion.

21. The process according to claim 1, wherein the zeolite is offretite/erionite which is cation exchanged with zinc ion.

22. The process according to claim 1, wherein the zeolite is ZSM-5 cation which is exchanged with zinc ion.

23. The process according to claim 1, wherein the zeolite is mordenite which is cation exchanged with zinc ion.

24. The process according to claim 1, wherein the zeolite is zeolite L which is cation exchanged with zinc ion.

\* \* \* \* \*

UNITED STATES PATENT AND TRADEMARK OFFICE
CERTIFICATE OF CORRECTION

PATENT NO. : 5,574,172
DATED : November 12, 1996
INVENTOR(S) : KATSURO et al

It is certified that error appears in the above-identified patent and that said letters patent is hereby corrected as shown below:

Column 12, claim 13, delete "400°C" insert --200°C--.

Signed and Sealed this

Twenty-second Day of April, 1997

Attest:

BRUCE LEHMAN

*Commissioner of Patents and Trademarks*

*Attesting Officer*